United States Patent
Pasquantonio et al.

(10) Patent No.: US 6,641,396 B2
(45) Date of Patent: Nov. 4, 2003

(54) METHOD AND DEVICE FOR PREPARING THE HARD STRUCTURES OF TEETH FOR THE APPLICATION OF DENTAL RESTORATIVE MATERIALS

(76) Inventors: Guido Pasquantonio, Via Gregoriana, 12 - 00187 Rome (IT); Lorenzo Breschi, Via del Cappello, 4 - 40065 Pianoro (Bologna) (IT); Andrea Petrone, Via S. Felicola, 18 - 00134 Rome (IT)

(*) Notice: Subject to any disclaimer, the term of this patent is extended or adjusted under 35 U.S.C. 154(b) by 0 days.

(21) Appl. No.: 09/973,879

(22) Filed: Oct. 11, 2001

(65) Prior Publication Data

US 2003/0003422 A1 Jan. 2, 2003

(30) Foreign Application Priority Data

Jun. 29, 2001 (IT) .................................. BO2001A000418

(51) Int. Cl.[7] .................................................. A61C 5/06
(52) U.S. Cl. ...................................... 433/217.1; 433/32
(58) Field of Search ............................... 433/32, 217.1, 433/215, 226, 229

(56) References Cited

U.S. PATENT DOCUMENTS

| | | | |
|---|---|---|---|
| 1,509,161 A | * | 9/1924 | Maurer |
| 1,713,971 A | * | 5/1929 | Lowry et al. |
| 3,019,787 A | * | 2/1962 | Simmons |
| 3,048,170 A | * | 8/1962 | Lemos |
| 3,207,161 A | * | 9/1965 | Dietz |
| 3,292,620 A | * | 12/1966 | Mahler |
| 3,660,901 A | * | 5/1972 | Inoue |
| 3,716,054 A | * | 2/1973 | Porter et al. |
| 3,901,216 A | * | 8/1975 | Felger |
| 3,926,646 A | * | 12/1975 | Inoue |
| 4,149,533 A | * | 4/1979 | Ishkawa et al. |
| 4,164,214 A | * | 8/1979 | Stark et al. |
| 4,324,630 A | * | 4/1982 | Sugita et al. |
| 4,495,045 A | * | 1/1985 | Jackson |
| 6,090,053 A | * | 7/2000 | Ruetschi et al. |
| 6,202,897 B1 | | 3/2001 | Martin et al. |

FOREIGN PATENT DOCUMENTS

| | | |
|---|---|---|
| EP | 1027876 | 8/2000 |
| FR | 2656791 | 7/1991 |

* cited by examiner

Primary Examiner—Ralph A. Lewis
(74) Attorney, Agent, or Firm—Davidson Berquist Klima & Jackson, LLP

(57) ABSTRACT

A method and device for preparing the hard structures of teeth for the application of dental restorative materials, according to which, after a step of mechanical treatment to remove a layer of tissue from the hard structure of the tooth, at a given zone affected by a disorder, and after removing the debris generated by such treatment, a layer of an adhesive substance is spread over the zone using an application head connected by a wire in a support handpiece to a control power circuit able to generate electrical signals which subject the given zone to a difference in potential which subjects the adhesive substance to an electrokinetic force due to the passage of an electrical current able to move the adhesive substance in an even and deep way inside dentinal tubules and so that it occupies the irregular surface of the tooth enamel.

24 Claims, 3 Drawing Sheets

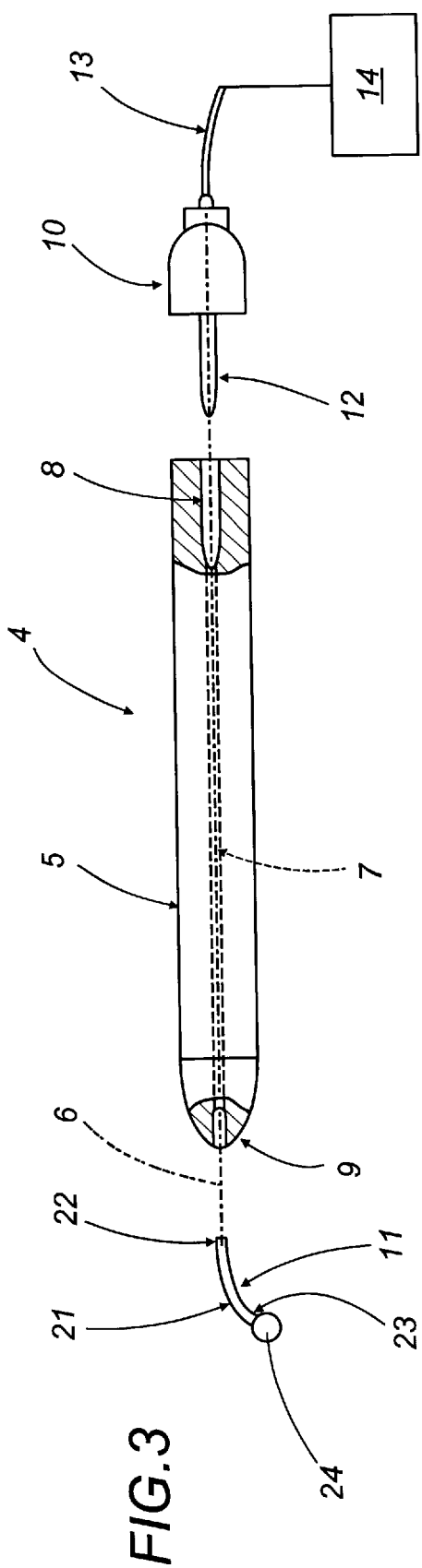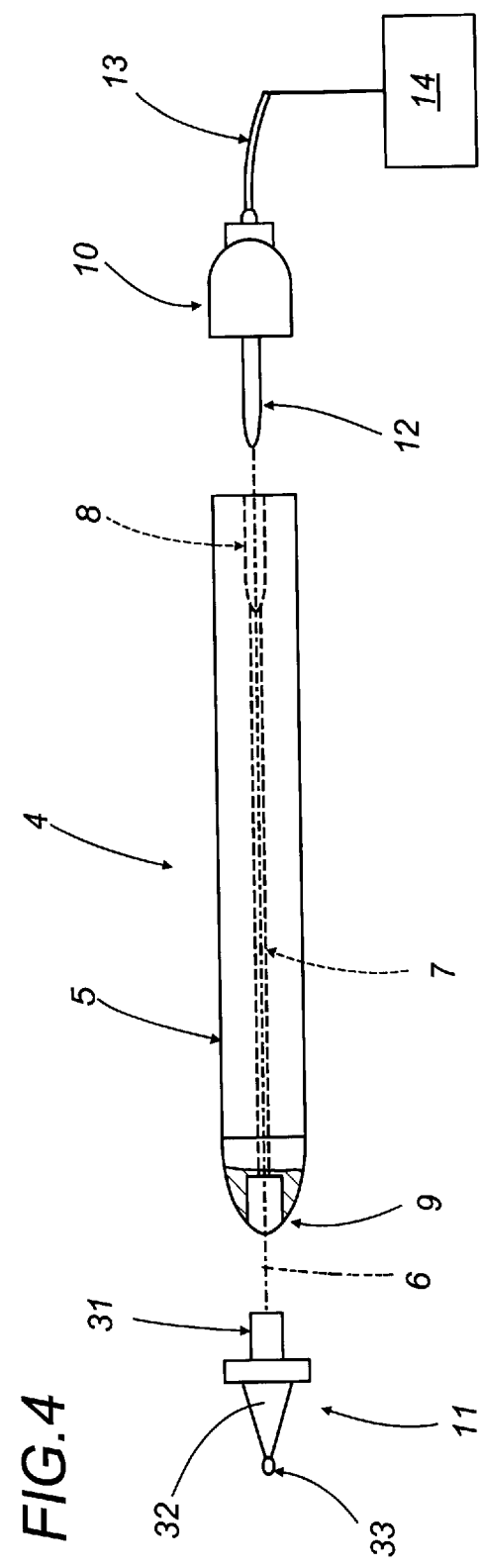

METHOD AND DEVICE FOR PREPARING THE HARD STRUCTURES OF TEETH FOR THE APPLICATION OF DENTAL RESTORATIVE MATERIALS

BACKGROUND OF THE INVENTION

The present invention relates to a method for preparing the hard structures of teeth for the application of dental restorative materials.

The adhesion of the dental restorative materials to the hard structures of the tooth, mainly enamel and dentin, is of paramount importance for dental preservation techniques.

The use, for example, of compound resins for tooth reconstruction has significantly increased due to the extremely high esthetic requirements of today's population. However, such resins have an unwanted secondary feature due to their polymerization, which is a significant contraction causing them to be detached from the tooth. For this reason or for obvious retention requirements in preparations which are not self-retaining, adhesive substances must be used, which allow a bond between the mineralized tissues of the teeth and the compound resins. Therefore, the adhesive should perform the essential function for the success of the reconstruction, guaranteeing a marginal seal for the restoration made of compound resin.

To increase the retentive capacity of the substrate, for many years the treatment of dentin and enamel with various acidic solutions (or gels) was recommended. Such a process is called acid-etching and has a variety of different functions, depending on the tissue to which it is applied. On enamel, acid-etching makes the surface more receptive to the above-mentioned adhesive, dissolving the mineralized surface layer and revealing a rough, uneven surface. This surface is characterized by alternating so-called "enamel prisms", that is to say, crystalline structures with varying orientation which guarantee that the adhesive resin can penetrate in small grooves and form interdigitations which guarantee retention and sealing. In practice, the fluid resin of the adhesive fills the microporosities in the enamel, guaranteeing micro-mechanical retention which allows the seal. Moreover, acid-etching increases the wettability of the enamel and allows the adhesive an angle of contact optimum for complete integration.

Dentin adhesion presents numerous problems because it has a different structure from enamel. Dentin consists not only of a mineral (hydroxyapatite) like enamel (in which 97% is mineral substance), but also an organic substance, that is to say, collagen fibrils which do not easily attach to acrylic hydrophobic resins. Moreover, dentin has a high water content, a factor which makes the sticking process even more complex.

In particular, dentin is a tissue characterized by a plurality of tubules which join the inside of the tooth (pulp) and the peripheral dentin. Inside these tubules there are the so-called "odontoblastic processes", that is to say, the cellular extensions of pulp cells (odontoblasts) hydrated by the fluid from blood circulation. Each tubule is surrounded by a hood of hypermineralized dentin, called the peritubular dentin. The dentin between one tubule and another is called intra-tubular, is very fibrous and less mineralized. The tubules are arranged radially starting from the pulp and have a decreasing diameter, therefore, their density differs according to the dentinal zone in which they are located and, therefore, the adhesion substrate changes according to the zones.

When the dentin is treated at given affected zones by removing the layer of tissue affected by the disorder, for example it is treated with a manual or rotary instrument to remove the decayed process or to prepare a cavity, a layer of debris called the "smear layer" is produced, which occludes the orifices of the dentinal tubules and covers the intertubular dentin, reducing its permeability.

The application of an etching acid on the dentin previously treated, therefore, removes the layer of debris, re-opening the dentinal tubules and demineralizing the top layer of dentin, removing the mineral part and leaving the organic matrix.

The process of demineralizing the surface of the dentin takes place both at intertubular and peritubular level, although the degree of incisiveness varies given the different levels of mineralization of the two structures. In particular, the tubules at the surface on which the etching acid was passed widen to a funnel shape and over the first 4 or 5 microns of thickness the intra-tubular tissues are completely demineralized, leaving only collagen fibrils.

These collagen fibrils, when in their so-called wet state, are porous, whilst when they are dry they collapse upon themselves and are reduced to a compact tissue on which, in contrast to the porous tissue, it is extremely difficult for the adhesive substances to stick.

At this point, the main problem of adhesion on the dentin is succeeding in completely penetrating the demineralized layer and entering several microns into the tubules so as to guarantee an effective seal. If part of the organic matrix is not reached by the fluid resin of the adhesive and remains exposed, it is rapidly degraded by salivary enzymes, forming a marginal gap at the sides of the restorative work.

Various methods of correctly infiltrating the dentin have been put forward, mainly aiming to keep the collagen fibrils (organic matrix exposed by acid-etching) from collapsing and to allow the adhesive to pass to the deepest zones.

Adhesive substances have been used which consist mainly of an acid-etching solution (mainly phosphoric acid 30–40%) and a polymerizable solution of hydrophilic and hydrophobic monomers. When the acid is washed away from the surface of the enamel and dentin, the monomer solution is applied (even in several layers) to the etched surface of the tooth. The most modern adhesives use acetone or ethanol as a solvent. The function of the solvent is to remove and substitute the water from the demineralized dentinal matrix.

The adhesive molecules have two functional groups: one with a great affinity for the surface of the tooth (hydrophilic) and another with the resinous material (hydrophobic) which is put over the layer of adhesive. The hydrophilic monomer which constitutes the main part of the adhesives is able to create micro-mechanical retention by interpenetrating the collagen fibrils exposed by the acid-etching, forming a mixed structure of organic matrix, inorganic residues and resin called the hybrid layer.

Formation of the hybrid layer still appears essential in order to guarantee a good degree of sealing. Moreover, the adhesive which enters the tubules which are open and widened to a funnel shape by the acid-etching process guarantees retention by forming resin extensions.

The absence of a seal can allow the infiltration of bacteria which may cause secondary decay under the reconstruction, which leads to rapid failure of the therapy. Also, it has been noticed that most breaks and yielding occur at the hybrid layer level, since complete impregnation with the resin is not achieved.

More specifically, the generation of zones which are not infiltrated seems to be the result of a variety of factors, including, for example, an acid-etching step which is too aggressive and demineralizes the fibrils too deep, so that where they are not reached by the resin, the fibrils are completely dried out and collapse, forming a compact layer which is difficult to infiltrate and an irreversible denaturation and, therefore, modification of the collagen fibrils following acid-etching or drying or cutter overheating.

All of these factors contribute to the creation of a layer which is not completely impregnated and with various microporosities which allow the passage of enzymes and bacteria.

It is, therefore, evident how the weak point of the entire adhesive process is guaranteeing precision filling of the open tubules after the acid-etching and complete infiltration of the collagen fibril matrix for a correct seal.

The aim of the present invention is to overcome the above-mentioned disadvantages to guarantee complete adhesion of the adhesive substances on the hard structures of the tooth.

SUMMARY OF THE INVENTION

Accordingly, the present invention provides a method for preparing the hard structures of teeth for the application of dental restorative material, characterized in that it comprises steps of treating at least one affected zone of the hard structure of the tooth, removing the layer of tissue affected by the disorder, applying a layer of adhesive substance at least in the zone treated, subjecting at least the adhesive substance to the action of an electrical field, applying the restorative material at least on the zone covered by the adhesive substance. The present invention also relates to a device for preparing the hard structures of teeth for the application of dental restorative materials.

In accordance with the present invention, a device is provided which prepares the hard structures of teeth for the application of dental restorative materials, characterized in that it comprises at least one handpiece connected to a control power circuit for applying an electrical field to at least one layer of adhesive substance, applied at least to an affected zone of the hard structure of the tooth, previously treated to remove the layer of tissue affected by the disorder, so as to apply the restorative material at least on the zone covered by the layer of adhesive substance.

BRIEF DESCRIPTION OF THE DRAWINGS

The technical characteristics of the invention, in accordance with the aims, are clearly described in the claims herein and the advantages are apparent from the detailed description which follows, with reference to the accompanying drawings, which illustrate a preferred embodiment of the invention, without limiting the scope of application, and in which:

FIG. 3 is an exploded schematic side view of a first preferred embodiment of a handpiece which is part of the device illustrated in FIG. 1;

FIG. 4 is a schematic side view of a second preferred embodiment of a detail from FIG. 3;

DESCRIPTION OF THE PREFERRED EMBODIMENTS

Figure 1:
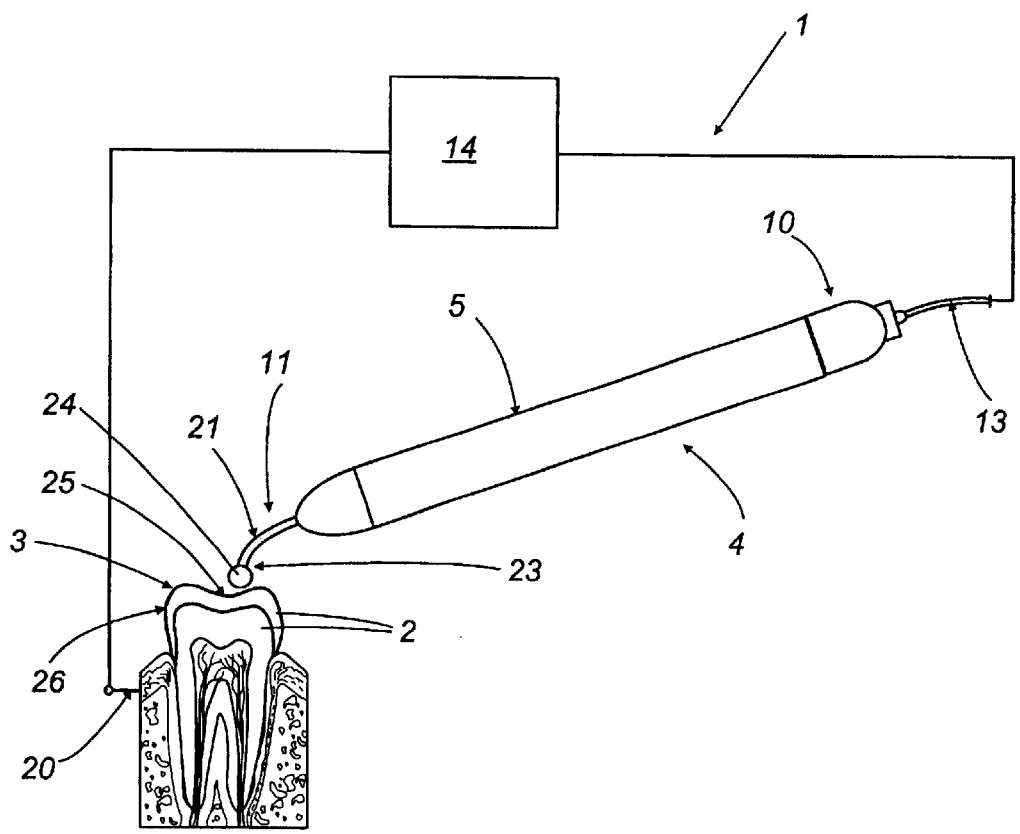
FIG. 1 is a schematic side view of a device for preparing the hard structures of teeth for the application of dental restorative materials.
Figure 2:
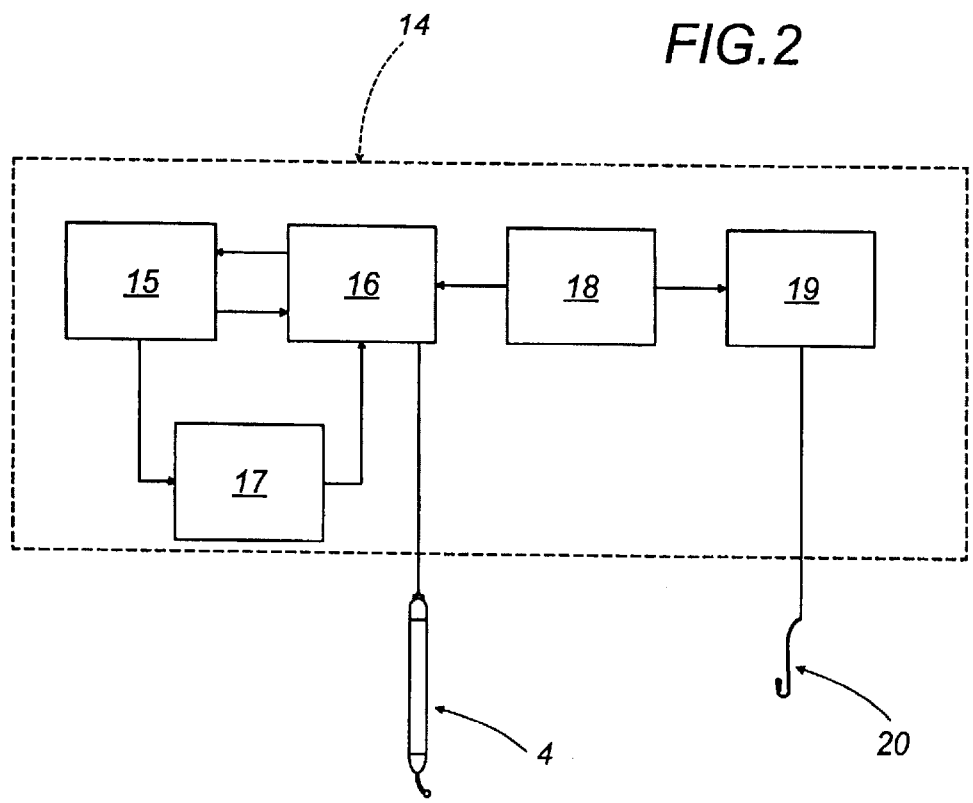
FIG. 2 is a block diagram of a power and control circuit to which the device illustrated in FIG. 1 is connected.
Figure 5:
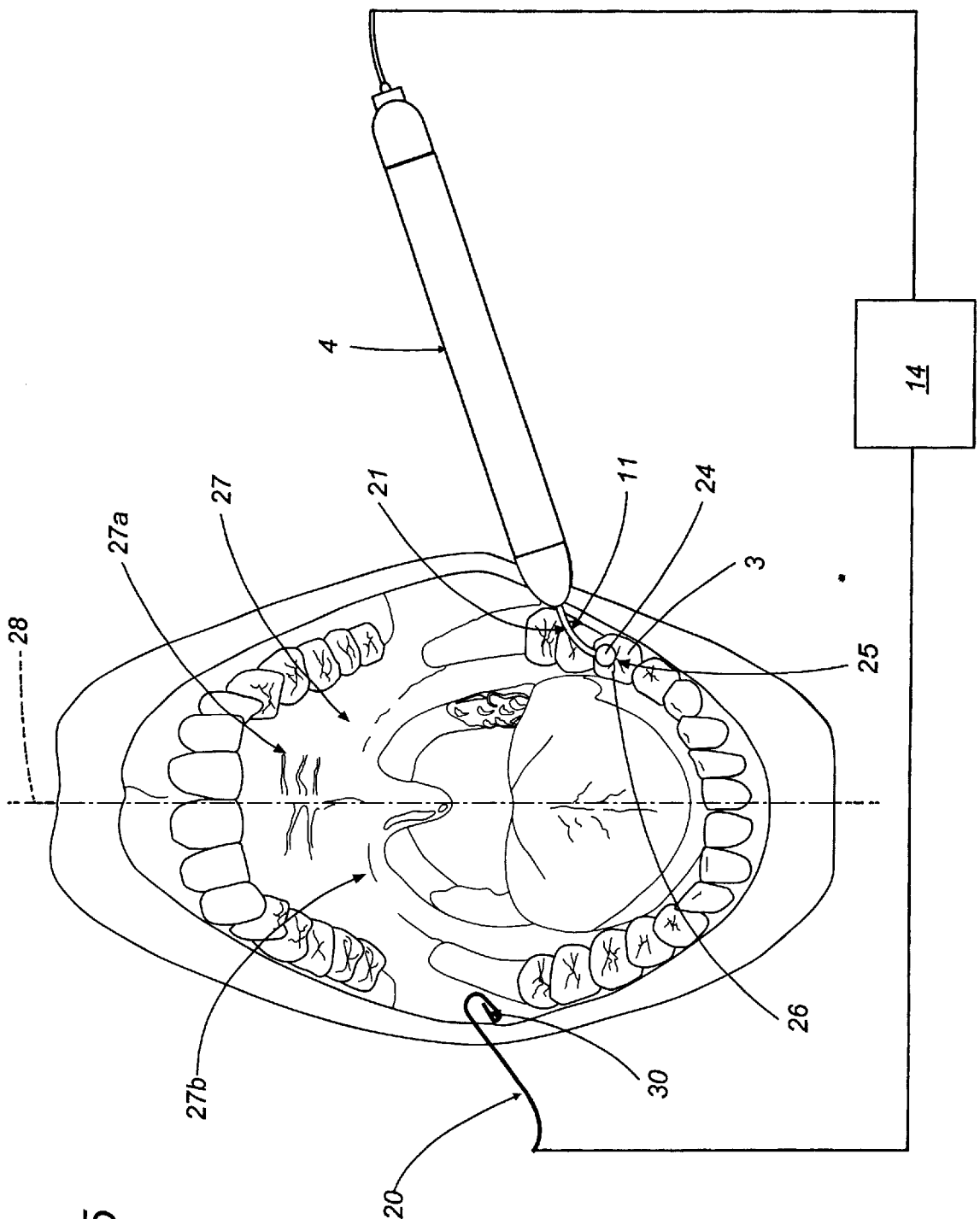
FIG. 5 is a schematic front view of the device in FIG. 1 operating inside the mouth of a patient.

With reference to FIGS. 1, 2 and 5, the numeral 1 denotes as a whole a device for preparing the hard structures 2 of teeth 3 for the application of dental restorative materials, such as monomers, compound resins and similar products of the known type and widely used in the sector of dental restoration and reconstruction.

The device 1 comprises a handpiece 4 which has a substantially tubular central grip 5 with longitudinal axis 6, the outside made of an insulating material, for example silicone rubber and similar materials, which allows the operator a good grip. Inside the grip, in a substantially coaxial position, there is a wire 7 connected to the two opposite ends of the grip with a first and a second socket (female), respectively labeled 8 and 9, of the known type and designed to receive in a removable fashion, that is to say, in such a way that it can be easily attached and removed, a connector 10 and a connection and application head 11 whose use and operation are described below.

The connector 10 has a plug 12 designed for insertion in the first socket 8 and is electrically connected, by an electrical cable 13, to a control power circuit, labeled 14 as a whole. The circuit 14 comprises a control block 15 connected at its output to an amplifier block 16 and a signal generator 17, which is in turn connected at its output to the amplifier 16 which leads back to the control block 15. The amplifier 16 input is connected to a battery 18 which is in turn connected to a command block 19, whilst the amplifier 16 output is connected directly to the connector 10. The command block is connected to an electrode 20 which can be inserted in the patient's mouth. The latter is normally called an intra-oral electrode.

The circuit 14 is designed to power the handpiece 4 with an operating voltage which may reach values of 200 Volts, and with a current which can reach values of around 40 A.

Obviously, the electrical power supply may be direct or alternating. If alternating, the operating frequency may reach around 1 GHz.

The above-mentioned connection and application head 11, once applied to the end 9 of the handpiece is designed to be electrically connected to the circuit 14 and, therefore, is designed to become an electrical distributor of the electrical power sent from the block 17 which can send direct or alternating signals, of sinusoidal, square wave, triangular ramp, step, pulse train and similar types.

In the embodiment illustrated in FIGS. 1, 2 and 3, the head 11 comprises a metal insert 21, one end 22 of which is designed for insertion, like a plug, in the second socket 9, to guarantee an electrical contact with the wire 7 in the grip 5, whilst the other end 23 supports means 29 for moving the adhesive substance which may be a sponge, a brush or similar item. In FIGS. 1, 2 and 3, the means 29 for moving the substance consist of a sponge 24 or similar means able to retain a substance and then release it every time it makes contact with the surface. Once the circuit 14 has been activated and when the head 11 has been moved towards a given zone 25 of the surface 26 of the hard structure 2 of a tooth 3, the device 1 can subject the zone 25 to an electrical field. As illustrated in FIGS. 1 and 5, the method for preparing the hard structure 2 of a toot 3, inside a patient's mouth 27 for receiving restorative materials, using the device 1, comprises steps of treating at least the given zone 25 which is obviously affected, for example attached by a bacterial and inflammatory process such as decay and similar disorders. The treatment is normally of the mechanical type, and is carried out using tools such as dental burrs and drills able to remove the layer of tissue, of the hard structure 2 of the tooth 3, affected by the disorder. Once this treatment has been carried out, the layer of debris produced during the previous mechanical treatment step is removed, in order to re-open the dentinal tubules. At this point, the operator brings the end 23 of the metal insert 21 in the head 11 into contact with the given zone 25, taking care to first soak up a suitable primer adhesive substance with the sponge 24. When the sponge 24 arrives at the given zone 25 of the surface 26 of the hard structure 2 of a tooth 3, the operator uses the block 19 to activate the circuit 14, which uses the generator 17 to send an electrical signal to the handpiece 4 which, through the wire 7, reaches the insert 21. In this way, an electrical field is created on the Zone 25 and the adhesive substance is subjected to a difference in potential, after ensuing that the electrode 20 is positioned at a point 30 on the patient's body, for example in the mouth 27. This creates an electrokinetic force at the zone 25 covered by the layer of adhesive material, able to move the adhesive substance evenly and deeply towards the innermost layers of the hard structure 2 of the tooth 3. In this way, the adhesive substance, moved by the passage of electrical charges, is distributed deep down inside the dentinal microtubules and covers the irregular surface of the tooth 3 enamel. At this point the operator distributes a layer of adhesive resin restorative material on the zone 25 on which the primer adhesive substance was distributed, forming a structure for retaining the restorative material, without the disadvantages previously mentioned.

As indicated above, the electrode 20 may be applied to any area of the patient's body. Advantageously, as illustrated in FIG. 5, the electrode 20 may be applied in the mouth 27. In FIG. 5, for a clearer description, the mouth 27 is divided into two parts 27a and 27b by a substantially symmetrical plane 28. The electrode 20 may be placed at a point 30 in a position on the side opposite the handpiece 4. In other words, to work on a tooth 3 in the part 27a of the mouth, the electrode 20 must be placed at the point 30 on the part 27b, as illustrated in FIG. 5. Vice versa, to work on a tooth 3 in the part 27b of the mouth, the electrode 20 must be placed at the point 30 on the part 27a.

In the embodiment illustrated in FIG. 4, the head 11 may be made in such a way that it has a connecting portion 31 in the socket 9, a tank 32 for holding a given amount of the adhesive substance, and a point 33 for distribution of the adhesive substance. The point constitutes the means 29 for moving the adhesive substance. The method for the application of the adhesive substance is identical to that previously described relative to the embodiment illustrated in FIG. 3.

It must be emphasized that for both embodiments illustrated the head 11 is of the single-use type and can be substituted for each application cycle.

The invention described can be subject to numerous modifications and variations without thereby departing from the scope of the inventive concept. Moreover, all the details of the invention may be substituted by technically equivalent elements.

What is claimed is:

1. A method for preparing the hard structures of teeth for the application of dental restorative materials, comprising:
   treating at least an affected zone of the hard structure of the tooth,
   removing the layer of tissue affected by the disorder,
   applying a layer of an adhesive substance of a dental bonding system to the zone treated, the adhesive substance comprising at least one of a primer and an adhesive resin, the primer having an affinity for both the tooth structure and the adhesive resin and
   subjecting at least the adhesive substance to the action of an electrical field.

2. The method according to claim 1, wherein the step of generating an electrical field includes the application of a difference in potential between the zone treated and covered by the adhesive substance and a given point of the patient's body so as to generate, at least at the zone treated, an electrokinetic force due to the passage of an electrical current able to move the adhesive substance in an even, deep way inside the dentinal tubules and such that it covers the irregular surface of the enamel on the tooth.

3. The method according to claim 1, wherein the steps of applying a layer of adhesive substance and subjecting the adhesive substance to the action of an electrical field take place simultaneously and the layer of adhesive substance is applied while subjecting the layer of adhesive substance to the electrical field.

4. The method according to claim 3, further comprising a step of removing the layer of debris deriving from the treatment of the affected zone, so as to re-open the dentinal tubules.

5. The method according to claim 4, further comprising a step of demineralizing the surface layer of the dentin on the tooth, removing the mineral part and leaving the organic matrix.

6. The method according to claim 5, further comprising a step of applying the restorative material at least on the zone covered by the layer of adhesive substance.

7. The method according to claim 6, wherein the electrical field is produced by a voltage of not greater than 200 Volts.

8. The method according to claim 7, wherein the two electrical quantities, voltage and current, are direct.

9. The method according to claim 7, wherein the two electrical quantities, voltage and current, are alternating and have an operating frequency of no greater than 1 GHz.

10. The method according to claim 6, wherein the electrical field is produced by a current of not greater than 40 A.

11. The method according to claim 1, wherein the step of subjecting the adhesive substance to the action of an electrical field is carried out using a handpiece connected to a control power circuit, also connected to an electrode designed to be placed at any given point on the patient's body.

12. The method according to claim 11, wherein the step of applying the layer of adhesive substance is carried out using the handpiece comprising an application head.

13. The method according to claim 12, wherein the application head comprises means for containing and distributing the adhesive substance.

14. The method according to claim 13, wherein the containing and distributing means comprise a metal insert, one end of which bears a means for moving the adhesive substance at least on the zone treated.

15. The method according to claim 14, wherein the means for moving the adhesive substance comprises a sponge-like element designed to soak up the adhesive substance and to be passed over the zone treated in order to apply a layer of the adhesive substance at least on the zone treated.

16. The method according to claim 11, wherein the electrode is an intra-oral electrode and is designed to be placed in the side of the mouth opposite that of the tooth on which the adhesive substance must be applied.

17. The method according to claim 16, wherein the application head is of a disposable type.

18. A device for preparing the hard structures of teeth for the application of dental restorative materials over an adhesive substance of a dental bonding system, comprising:

at least one handpiece connected to a control power circuit for applying an electrical field to at least one layer of the adhesive substance of the dental bonding system applied at least to an affected zone of the hard structure of the tooth previously treated to remove the layer of tissue affected by the disorder, the control power circuit constructed and arranged for operative connection to the hard structure of the tooth; and an electrode connected to the control power circuit and designed to be placed at any given point on the patient's body and operating in conjunction with the handpiece to apply a difference in potential between the zone treated and covered with the layer of adhesive substance and the given point of application of the electrode, thus generating, at least at the zone treated, an electrokinetic force due to the passage of electrical current able to move the adhesive substance in an even, deep way within the dentinal micro-tubules, so that it covers the irregular surface of the enamel of the tooth.

19. The device according to claim 18, wherein the electrode is an intra-oral electrode and is designed to be placed in the side of the mouth opposite that of the tooth on which the dental restorative material must be applied.

20. The device according to claim 18, wherein the handpiece comprises an application head for the layer of adhesive substance able to subject the adhesive substance to the action of the electrical field during its application to the zone treated.

21. The device according to claim 20, wherein the application head comprises means for containing and distributing the adhesive substance.

22. The device according to claim 21, wherein the containing and distributing means comprise a metal insert, one end of the insert bearing means for moving the adhesive substance at least on the zone treated.

23. The device according to claim 22, wherein the means for moving the adhesive substance comprises a sponge-like element designed to soak up the adhesive substance and to be passed over the zone treated, applying a layer of adhesive substance at least on the zone treated.

24. The device according to claim 23, wherein the application head is of a disposable type.

* * * * *